US010456286B2

(12) United States Patent
Plecnik et al.

(10) Patent No.: US 10,456,286 B2
(45) Date of Patent: Oct. 29, 2019

(54) TORQUE-COMPENSATING ASSISTIVE WRIST BRACES

(71) Applicant: The Regents of the University of California, Oakland, CA (US)

(72) Inventors: Mark M. Plecnik, Irvine, CA (US); Derek Bissell, Irvine, CA (US); David Reinkensmeyer, Irvine, CA (US); J. Michael McCarthy, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 497 days.

(21) Appl. No.: 15/269,773

(22) Filed: Sep. 19, 2016

(65) Prior Publication Data

US 2017/0079825 A1 Mar. 23, 2017

Related U.S. Application Data

(60) Provisional application No. 62/219,957, filed on Sep. 17, 2015.

(51) Int. Cl.
*A61F 5/01* (2006.01)
*A61H 1/02* (2006.01)

(52) U.S. Cl.
CPC ...... *A61F 5/013* (2013.01); *A61F 2005/0144* (2013.01); *A61F 2005/0169* (2013.01); *A61F 2005/0179* (2013.01); *A61H 1/0285* (2013.01)

(58) Field of Classification Search
CPC ............ A61F 5/013; A61F 2005/0144; A61H 1/0285
See application file for complete search history.

(56) References Cited

U.S. PATENT DOCUMENTS

| | | | | |
|---|---|---|---|---|
| 3,707,963 A * | 1/1973 | Keropian | A61F 5/013 601/40 |
| 5,002,044 A * | 3/1991 | Carter | A61F 5/013 602/16 |
| 5,503,619 A * | 4/1996 | Bonutti | A61F 5/013 601/33 |
| 5,853,680 A | 12/1998 | Iijima et al. | |
| 5,891,061 A * | 4/1999 | Kaiser | A61F 5/0125 601/33 |
| 6,093,162 A * | 7/2000 | Fairleigh | A61F 5/013 602/22 |

(Continued)

OTHER PUBLICATIONS

Balli, et al., "Defects in lilnk mechanisms and solution rectification", Mechanism and Machine Theory 37(0): 2002.

(Continued)

*Primary Examiner* — David H Willse
*Assistant Examiner* — Javier G Blanco
(74) *Attorney, Agent, or Firm* — Thomas | Horstemeyer, LLP

(57) ABSTRACT

In one embodiment, a torque-compensating assistive wrist brace includes a hand member adapted to be provided on a user's hand, a forearm member adapted to be provided on the user's forearm, and an assistive linkage that connects the hand and forearm members together and that applies a balancing torque to a wrist of the user that counteracts intrinsic stiffness within the wrist and assists the user in rotating the wrist in both the flexion and extension directions.

5 Claims, 14 Drawing Sheets

(56) References Cited

U.S. PATENT DOCUMENTS

| | | | | |
|---|---|---|---|---|
| 2010/0249948 A1* | 9/2010 | Kawakami | A61F 4/00 | 623/26 |
| 2010/0280423 A1* | 11/2010 | Kawakami | A61H 1/024 | 601/33 |
| 2011/0282253 A1* | 11/2011 | Menon | A61F 5/013 | 601/40 |
| 2013/0053741 A1* | 2/2013 | Pittaccio | A61F 5/0102 | 602/16 |
| 2014/0142483 A1* | 5/2014 | Jackson, Jr. | A61F 5/013 | 602/16 |

OTHER PUBLICATIONS

Bissell, Derek, Wrist (Wrist Resonator for Independent Stroke Training) Thesis, 2014.

Blackett, Ricardo, "Optimal synthesis of planar five-link mechanisms for the production of nonlinear mechanical advantage", Thesis; 2001.

Bulatavic, et al., "Improved cuckoo search (ICS) algorthm for constrained optimization problems", Mechanism and Machine Theory; 61: 1-13, 2013.

Chase, et al., "Circuits and branches of single-degree-of-freedom planar linkages", Journal of Mechanical Design, 115, 1993.

Dhingra, et al, "Synthesis of six-link, slider-crank and four-link mechanisms for function, path and motion generation using homotopy with m-homogenization", Journal of mechanical designs, 116(4), 1994.

Hwang, et al., "Defect-free synthesis of stephenson-II function generators", Journal of mechanisms and robotics, 2(4), 2010.

McLarnan, CW., "Synthesis of six-link plane mechanisms by numerical analysis", Journal of engineering for industry, 85, 1963.

Mirbagheri, et al., "Neuromuscular properties of different spastic human joints vary systematically", 32nd Annual International Conference of IEEE EMBS, 2010.

Plecnik, et al., "Numerical synthesis of six-bar link-ages for mechanical computation", ASME Journal of mechanisms and robotics, 6(3), 2014.

Plecnik, et al., "Computational design of stephenson II six-bar function generators for 11 accuracy points", ASME Journal of Mechanisms and Robotics, Mar. 2015.

Root, et al., "A survey of optimization methods applied to design of mechanisms", ASME, 1976.

Sancibrian, R. "Improved GRG method for the optimal synthesis of linkages in function generation problems", Mechanism and machine theory, 2011.

Shiakolas, et al., "On the optimum synthesis of six-bar linkages using differential evolution and the geometric centroid of precision positions technique", Mechanism and Machine Theory, 2005.

Simionescu, et al., "Four-and six-bar function cognates and overconstrained mechanisms", Mechanism and machine theory, 2001.

Simionescu, et al., "Synthesis of function generators using the method of increasing the degree of freedom of the mechanism", Proceedins Ninth World congress on the theory of machines and mechanisms, 1995.

Wampler, CW, "Isotropic coordinates, circularity, and bezout numbers: planar kinematics from a new perspective" 1996 ASME design engineering technical conference and computers, 1996.

* cited by examiner (a) $\Delta\phi$ is input (b) $\Delta\psi = f(\Delta\phi)$ (c) $\Delta\psi$ is input (d) $\Delta\phi = f(\Delta\psi)$

TORQUE-COMPENSATING ASSISTIVE WRIST BRACES

CROSS-REFERENCE TO RELATED APPLICATION

This application claims priority to U.S. Provisional Application Ser. No. 62/219,957, filed Sep. 17, 2015, which is hereby incorporated by reference herein in its entirety.

BACKGROUND

When a person suffers a stroke, one of the resulting physical impairments is wrist spasticity, which causes excessive wrist stiffness and resistance to stretch, known as "tone." Studies suggest that this increase in stiffness, or tone, may be due to changes in the wrist flexor and extensor muscles, which result in an increased torque demand to achieve wrist movement.

While devices have been developed that provide assistive force or torque to the wrist in flexion or extension to assist with wrist movement, such devices only provide assistance in one of these directions. Moreover, this assistance decreases as the angular rotation of the wrist increases, which is the opposite of what is needed given that rotation becomes more difficult as the angle of rotation increases. In view of this, it can be appreciated that it would be desirable to have a device that mitigates the intrinsic stiffness of stroke victim wrists and therefore provides assistance to the individual in bending the wrist in both flexion and extension, as well as holding a desired angular position.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

Figure 1:
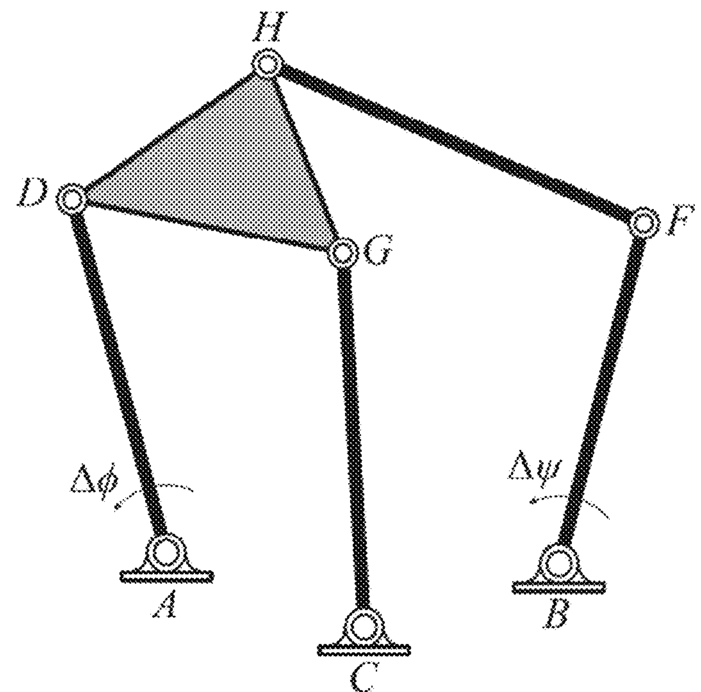
FIG. 1 is a schematic drawing of a Stephenson III six-bar function generator.

As described above, it would be desirable to have a device that mitigates the intrinsic stiffness of stroke victim wrists and therefore provides assistance to the individual in bending the wrist in both flexion and extension, as well as holding a desired angular position. Disclosed herein are torque-compensating assistive wrist braces that provide assistive torque that counteracts the increased torque that the intrinsic stiffness imposes. In some embodiments, the wrist brace comprises a hand member, a forearm member, and an assistive linkage that provides supporting forces between the hand and forearm members around the wrist in order to balance and cancel out the increased torque. This results in a reduction in effort required by the individual to achieve or hold a desired angular wrist position. In some embodiments, the linkage comprises a spring-actuated six-bar linkage that provides an angle-dependent supporting torque that balances the torque imposed by the wrist stiffness.

In the following disclosure, various specific embodiments are described. It is to be understood that those embodiments are example implementations of the disclosed inventions and that alternative embodiments are possible. All such embodiments are intended to fall within the scope of this disclosure.

As noted above, the disclosed wrist braces can comprise an assistive linkage that provides supporting forces between a hand member and a forearm member. In some embodiments, this linkage comprises a spring-assisted six-bar linkage. Described below is a direct solution of the kinematic synthesis equations for Stephenson III six-bar linkages that yield function generators that can achieve as many as 11 accuracy points. The synthesis equations yield thousands of candidate linkage designs that can be analyzed to identify those that achieve a required task in a single configuration and without passing through a singularity. This requires identification of the function generator cognates among the design candidates and a direct numerical analysis of each candidate design. It can happen that a cognate solution does not appear in the synthesis results due to numerical issues, in which case those cognates are constructed and added to the synthesis results. The result is a set of linkages that achieve the specified function generation task and are free of branch and circuit defects.

A six-bar linkage comprises four binary links, i.e., links having two joints or pivot points, and two ternary links, i.e., links having three joints or pivot points. These systems form two distinct topologies known as Watt and Stephenson six-bar linkages. The Stephenson six-bar linkages have the property that the two ternary links are separated by the binary links, while the Watt topology has the ternary links connected to each other.

The kinematic synthesis of six-bar function generators is an extension of the original work by Freudenstein (1954), in which the loop equations of the system are formulated in each of the configurations specified by the required input-output angles. The result is a set of polynomial equations that are solved to determine the dimensions of the linkage.

FIG. 1 shows a Stephenson III six-bar linkage having a ternary link as its ground link and two loops defined by joint coordinates: (i) ADGC and (ii) ADHFB. The ground pivots A and B are used as the centers of N coordinated angles $\phi_j$ and $\psi_j$, j=0, . . . , N−1. The joint angles of A and C are part of a four-bar sub-loop, which means their coordinated movement is defined by four-bar loop equations.

The planar kinematics of linkages is conveniently formulated using complex numbers. The scale, orientation, and location of a reference configuration for the linkage is defined in the plane by selecting A=0+0i and D=1+0i. The coordinates of the remaining joints B, C, F, G and H are calculated by solving the synthesis equations.

Figure 2A:
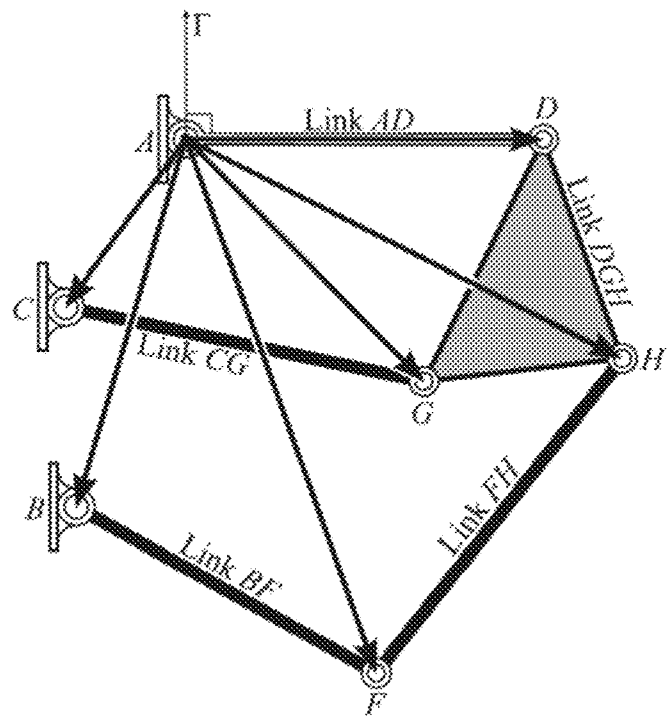
FIG. 2A is a schematic drawing of the reference configuration for the synthesis of a Stephenson III function generator.
Figure 2B:
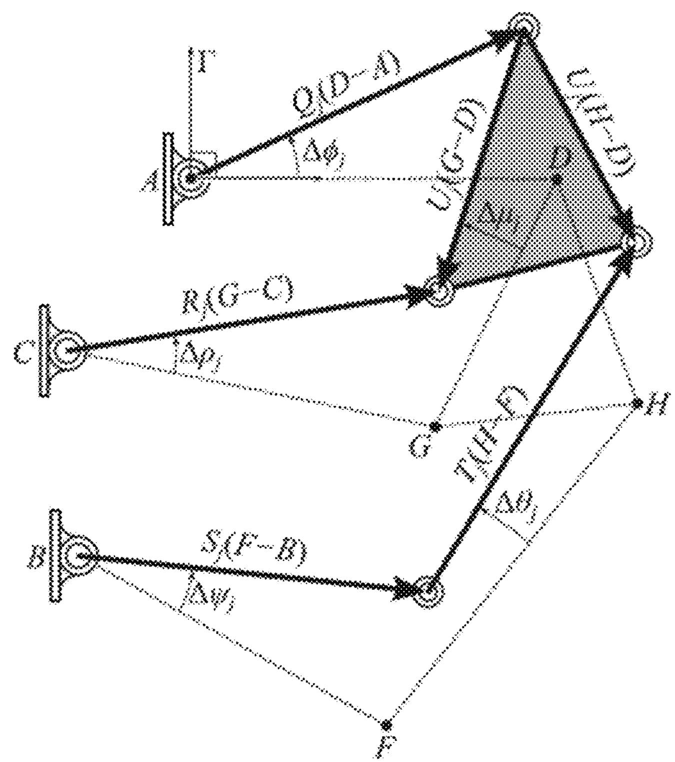
FIG. 2B is a schematic drawing of specified angles of the Stephenson III function generator measured relative to the reference configuration.

Introduce $(\Delta\phi_j, \Delta\psi_j)$, j=1, . . . , N−1 as the required input-output angles measured from the reference configuration (FIG. 2A), where $$(\Delta\phi_j,\Delta\psi_j)=(\phi_j-\phi_0,\psi j-\psi_0),\ j=1,\ \ldots,N-1. \tag{1}$$

The synthesis equations for the Stephenson III linkage are formed from the loop equations for each set of specified input-output angles.

The coordinates of the moving pivots of the linkage in each task configuration are related to their coordinates in the reference configuration by the equations, $$D_j=A+e^{\Delta\varphi j}(D-A),$$

$$F_j=B+e^{\Delta\psi j}(F-B),$$

$$G_j=A+e^{\Delta\varphi j}(D-A)+e^{\Delta\mu j}(G-D),$$

$$H_j=A+e^{\Delta\varphi j}(D-A)+e^{\Delta\mu j}(H-D),\ j=1,\ \ldots,N-1. \tag{2}$$

For convenience, introduce the notation, $$Q_j=e^{i\Delta\varphi j},\ R_j=e^{i\Delta\rho j},\ S_j=e^{i\Delta\psi j},$$

$$T_j=e^{\Delta\Theta j},\ U_j=e^{\Delta\mu j},\ j=1,\ \ldots,N-1. \tag{3}$$

Notice that $Q_j$ and $S_j$ are defined by the required input-output angle pairs. The remaining joint angles are unknowns that satisfy the normalization conditions, $$R_j\overline{R}_j=1,\ T_j\overline{T}_j=1,\ U_j,\ \overline{U}_j=1,\ j=1,\ \ldots,N-1, \tag{4}$$

where the overbar denotes the complex conjugate.

The loop equations for the Stephenson III six-bar linkage are obtained by evaluating $G_j-C$ and $H_j-F_j$ relative to the initial configuration. This yields two sets of complex conjugate loop equations, $$L_j{:}R_j(G-C)=(A+Q_j(D-A)+U_j(G-D))-C,$$

$$\overline{R}_j(\overline{G}-\overline{C})=(\overline{A}+\overline{Q}_j(\overline{D}-\overline{A})+\overline{U}_j(\overline{G}-\overline{D}))-\overline{C},$$

$$j=1,\ \ldots,N-1,$$

$$M_j{:}T_j(H-F)=(A+Q_j(D-A)+U_j(H-D))-(B+S_j(F-B)),$$

$$\overline{T}_j(\overline{H}-\overline{F})=(\overline{A}+\overline{Q}_j(\overline{D}-\overline{A})+\overline{U}_j(\overline{H}-\overline{D}))-(\overline{B}+\overline{S}_j(\overline{F}-\overline{B})),$$

$$j=1,\ \ldots,N-1. \tag{5}$$

The loop equations $L_j$, $M_j$, and the normalization conditions of Equation (4) form 7(N−1) quadratic equations in the 2(5+3(N−1)) unknowns consisting of the pivots locations B, C, F, G, and H and the joint rotations $R_j$, $T_j$, and $U_j$ and their complex conjugates. The Stephenson III synthesis equations are similar in form to the Stephenson II and both can be solved for a maximum of N=11 positions to obtain 70 quadratic equations in 70 unknowns that yield a total degree of $2^{70}=1.18\times10^{21}$.

The 70 synthesis equations for the Stephenson III function generator can be reduced to 10 equations in 10 unknowns. This can be achieved by eliminating $R_j$ and $\overline{R}_j$ in the pairs of equations $L_j$ and then eliminating $T_j$ and $\overline{T}_j$ in the pairs of equations $M_j$ of Equation (5). Finally, the unknowns $U_j$ and $\overline{U}_j$ can be eliminated from the resulting sets of equations.

To simplify the presentation of this calculation, introduce the complex numbers, $$a=G-D,\ f=G-C,\ h=A-C,\ k=D-A,$$

$$c=H-D,\ g=H-F,\ m=A-B,\ o=-(F-B), \tag{6}$$

so the loop equations take the form $$Lj{:}h+Q_jk+U_ja-R_jf=0,$$

$$\overline{h}+\overline{Q}_j\overline{k}+\overline{U}_j\overline{a}-\overline{R}_j\overline{f}=0,\ j=1,\ \ldots,10,$$

$$M_j{:}m+Q_jk+U_jc+S_jo-T_jg=0,$$

$$\overline{m}+\overline{Q}_j\overline{k}+\overline{U}_j\overline{c}+\overline{S}_j\overline{o}-\overline{T}_j\overline{g}=0,\ j=1,\ \ldots,10. \tag{7}$$

Eliminate R and $\overline{R}_j$ in $L_j$ and $T_j$ and $\overline{T}_j$ in $M_j$ to obtain the pairs of equations, $$(h+Q_jk+U_ja)(\overline{h}+\overline{Q}_j\overline{k}+\overline{U}_j\overline{a})=f\overline{f},$$

$$(m+Q_jk+U_jc+S_jo)(\overline{m}+\overline{Q}_j\overline{k}+\overline{U}_j\overline{c}+\overline{S}_j\overline{o})=g\overline{g},\ j=1,\ \ldots\ 10. \tag{8}$$

These 10 pairs of equations are linear in $U_j$ and $\overline{U}_j$, and can be written in the form, $$\begin{bmatrix} a\overline{b}_j & \overline{a}b_j \\ c\overline{d}_j & \overline{c}d_j \end{bmatrix}\begin{Bmatrix} U_j \\ \overline{U}_j \end{Bmatrix}=\begin{Bmatrix} \overline{f}f-a\overline{a}-b_j\overline{b}_j \\ g\overline{g}-a\overline{a}-d_j\overline{d}_j \end{Bmatrix},\ j=1,\ \ldots\ ,10. \tag{9}$$

where the complex numbers $b_j=D_j-C$ and $d_j=D_j-F_j$, given by $$b_j=h+Q_jk,$$

$$d_j=m+Q_jk+S_jo,\ j=1,\ \ldots,10, \tag{10}$$

are introduced to simplify the presentation of these equations.

Eliminate $U_j$ and $\overline{U}_j$ between the pairs of Equation (9) in order to obtain, $$\begin{vmatrix} a\overline{b}_j\overline{f}f-a\overline{a}-b_j\overline{b}_j \\ c\overline{d}_jg\overline{g}-c\overline{c}-d_j\overline{d}_j \end{vmatrix}\begin{vmatrix} \overline{a}b_j\overline{f}f-a\overline{a}-b_j\overline{b}_j \\ \overline{c}d_jg\overline{g}-c\overline{c}-d_j\overline{d}_j \end{vmatrix}+\begin{vmatrix} a\overline{b}_j & \overline{a}d_j \\ c\overline{d}_j & \overline{c}d_j \end{vmatrix}^2=0 \tag{11}$$

$$j=1,\ \ldots\ 10$$

where the vertical bars denote the determinant.

The total degree of the polynomial system in Equations (11) is $810=1.07\times10^9$, which is a similar case for the Stephenson II linkage. However, the simpler form of Equation (10) allows for an additional reduction before employing a multihomogeneous root count.

In order to reduce the degree of the synthesis Equations (11), introduce the variables, $$r_1=a\bar{h},\ r_2=c\bar{m},\ r_3=c\bar{o},\ r_4=m\bar{o},$$

$$\bar{r}_1=\bar{a}h,\ \bar{r}_2=\bar{c}m,\ \bar{r}_3=\bar{c}o,\ \bar{r}_4=\bar{m}o. \quad (12)$$

This allows the expansion of the terms, $$a\bar{b}_j=r_1+a\bar{k}\bar{Q}_j,$$

$$c\bar{d}_j=r_2+c\bar{k}\bar{Q}_j+r_3\bar{S}_j,\ j=1,\ \ldots,10 \quad (13)$$

And similarly the rest of the terms in Equations (11) can be expanded using the additional identities f=a+h+k and g=c+k+m+o to find, $$\begin{aligned}\eta_j &= f\bar{f} - a\bar{a} - b_j\bar{b}_j, \quad (14)\\ &= r_2+\bar{r_2}+r_3+\bar{r_3}+r_4+\bar{r_4}+k(\bar{g}-\bar{k})+\bar{k}(g-k)-\\ &\quad r_4\bar{S}_j-\bar{r_4}S_j-kQ_j(\bar{m}+\bar{S}_j\bar{o})-\bar{k}\,\bar{Q}_j(m+S_jo),\ .\\ \chi_j &= g\bar{g}-a\bar{a}-d_j\bar{d}_j,\\ &= r_1+\bar{r_1}+k(\bar{f}-\bar{k})+\bar{k}(f-k)-h\bar{k}\,\bar{Q}_j-\bar{h}kQ_j,\\ j &= 1,\ \ldots\ ,10.\end{aligned}$$

See that k and $\bar{k}$ are known from the specified pivot locations and ($Q_j$, $S_j$), j=1, . . . , 10 are known from the task requirements. Equations (13) and (14) are linear in terms of the unknowns a, c, f, g, h, m, o, $r_1$, $r_2$, $r_3$, and $r_4$.

The synthesis Equations (11) can be now be written as, $$\begin{vmatrix} r_1+a\bar{k}\,\bar{Q}_j & n_j \\ r_2+c\bar{k}\,\bar{Q}_j+r_3\bar{S}_j & X_j \end{vmatrix}\begin{vmatrix} \bar{r_1}+\bar{a}kQ_j & n_j \\ \bar{r_2}+\bar{c}kQ_j+\bar{r_3}S_j & X_j \end{vmatrix}+ \quad (15)$$

$$\begin{vmatrix} r_1+a\bar{k}\,\bar{Q}_j & r_1+\bar{a}kQ_j \\ r_2+c\bar{k}\,\bar{Q}_j+r_3\bar{S}_j & \bar{r_2}+\bar{c}kQ_j+\bar{r_3}S_j \end{vmatrix}^2=0$$

$$j=1,\ \ldots\ ,10.$$

$$\begin{vmatrix} r_1+a\bar{k}\,\bar{Q}_j & n_j \\ r_2+c\bar{k}\,\bar{Q}_j+r_3\bar{S}_j & X_j \end{vmatrix}\begin{vmatrix} \bar{r_1}+\bar{a}kQ_j & n_j \\ r_2+\bar{c}kQ_j+r_3S_j & X_j \end{vmatrix}+$$

$$\begin{vmatrix} r_1+a\bar{k}\,\bar{Q}_j & r_1+\bar{a}kQ_j \\ r_2+c\bar{k}\,\bar{Q}_j+r_3\bar{S}_j & r_2+\bar{c}kQ_j+\bar{r_3}S_j \end{vmatrix}^2=0$$

$$j=1,\ \ldots\ ,10.$$

The result is a set of 10 quartic polynomials, which together with the eight quadratic polynomials (Equation (12)) yields a polynomial system of degree, $4^{10}2^8$=268, 435, 456.

However, the 18 unknowns in this polynomial system can be separated into the two homogeneous groups, $$\langle c,\bar{c},G,\bar{G},r_1,\bar{r}_1\rangle,\langle B,\bar{B},F,\bar{F},H,\bar{H},r_2,\bar{r}_2,r_3,\bar{r}_3,r_4,\bar{r}_4\rangle. \quad (16)$$

The number of roots of this system of equations can be calculated as the coefficient of $\alpha_1^6\alpha_2^{12}$ in the expansion of $$256\alpha_1^2\alpha_2^6(2\alpha_1+2\alpha_2)^{10} \quad (17)$$

which yields a multihomogeneous degree, 55,050,240. This is a significant reduction in the size of the polynomial homotopy needed to solve these synthesis equations.

The 18 synthesis Equations (12) and (15) were solved on the Gordon cluster at the San Diego Supercomputer Center of the XSEDE supercomputing network using the polynomial homotopy software Bertini. Rather than specify the requirements for a particular task, the input parameters, ($Q_j$, $S_j$), j=1, . . . , 10, were set to random complex numbers to create a numerically general system. Homotopy paths were tracked over 40 hours on 512×2.6 GHz cores. Nonsingular solutions were sorted by their Jacobian condition number of which 834,441 were found.

The roots for the general system need only be computed once and then can be used as startpoints for a parameter homotopy for any particular set of input parameters. The advantage of parameter homotopy is that nonsingular endpoints of a general system are used as startpoints of a specific system so that only 834,441 paths need to be tracked in order to find all nonsingular solutions of a that specific system.

The solutions of the synthesis equations are examined to determine those that have real values for the linkage dimensions. This is checked by ensuring the joint coordinate pairs $(B,\bar{B}),(C,\bar{C}),(F,\bar{F}),(G,\bar{G})$, and $(H,\bar{H})$ are complex conjugates.

Each design candidate is also evaluated to identify its cognate pair among the solutions to the synthesis equations, or to construct the cognate, if it does not appear among these solutions.

For every Stephenson III function generator, there exists one other Stephenson III function generator with link lengths of different ratios that produces the exact same function. In order to compute this function generator cognate for a Stephenson III linkage ABCDFGH, the linkage can be considered as a four-bar linkage ADGC that controls the motion of the RR dyad BF that is connected at H. The four-bar ADGC has two other path cognates that generate the same coupler curve at H, and one of these cognates has an input link that shares the same angular displacement $\Delta\varphi$ as Link AD throughout the motion of H. The Stephenson III function cognate is built from this four-bar path cognate.

Figure 3:
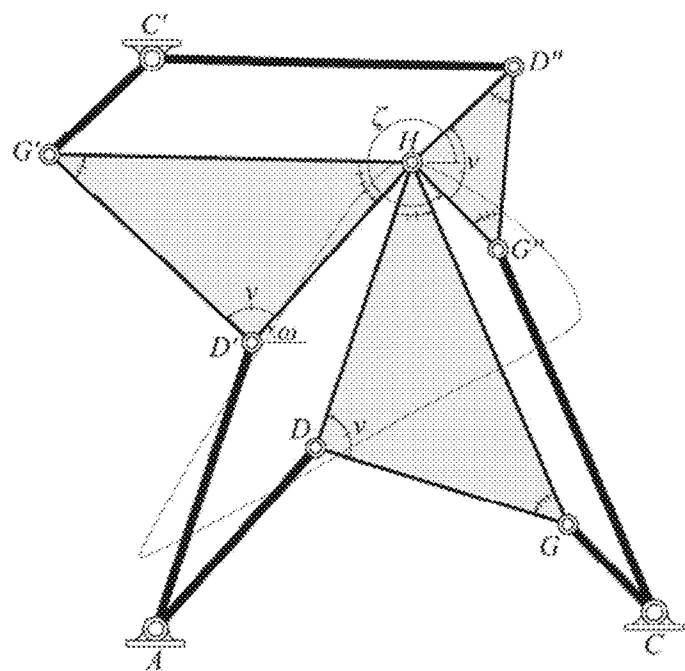
FIG. 3 is a schematic drawing of an overconstrained mechanism constructed from three four-bar curve cognates.
Figure 4:
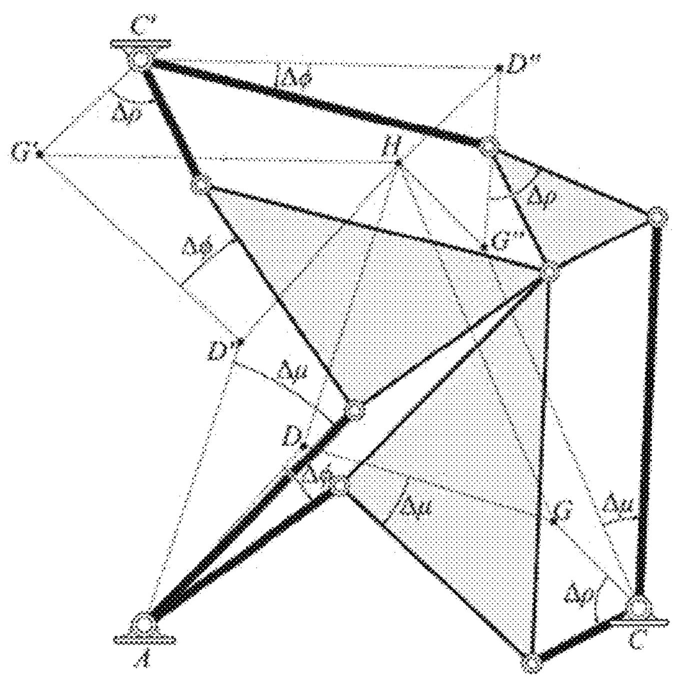
FIG. 4 is a schematic drawing of an overconstrained four-bar curve cognate mechanism shown in a displaced configuration.

The four-bar ADGC and its path cognates AD'G'C' and C'D"G"C are shown in FIG. 3 as an overconstrained mechanism that guides the point H. Note that Link C'D" of cognate linkage C'D"G"C shares the same angle $\Delta\phi$ with Link AD as shown in FIG. 4. Therefore, cognate linkage C'D"G"C can be connected to dyad BF at H to form a six-bar function cognate. The location of pivots C', D", and G" can be computed as $$C' = \frac{(A-D)(G-H)-(C-G)(D-H)}{(G-D)}+H, \quad (18)$$

$$D'' = \left(\frac{C-G}{D-G}\right)(D-H)+H,$$

$$G'' = C-G+H$$

However, the synthesis results only contain linkages with specified pivot locations A=0+0i and D=1+0i. So, for the sake of comparison, the cognate linkage must be scaled, rotated, and translates such that pivots C' and D" line up with pivots A and D. The transformation which computes this action on a point p is $$\Im(p) = \frac{D-A}{D''-C'}(p-C')+A \quad (19)$$

or equivalently, $$\Im(p) = \frac{D-G}{H-G}(p-C)+C \tag{20}$$

Applying $\Im$ to the cognate linkage, the coordinates of six-bar $(ABCDFGH)_c$ are $$\begin{aligned} A_c &= \Im(C') = A \\ B_c &= \Im(B) = \frac{D-G}{H-G}(B-C)+C \\ C_c &= \Im(C) = C \\ D_c &= \Im(D'') = D \\ F_c &= \Im(F) = \frac{D-G}{H-G}(F=C)+C \\ G_c &= \Im(G'') = D-G+C \\ H_c &= \Im(H) = \frac{D-G}{H-G}(H-C)+C \end{aligned} \tag{21}$$

Therefore, for every linkage solution {B, C, F, G, H} there should exist another solution $\{B_c, C_c, F_c, G_c, H_c\}$ in the synthesis results. If a missing cognate solution is detected, it is constructed and added to the results.

Once the design candidates have been sorted into cognate pairs, they are analyzed to evaluate the performance of each design. The criteria for a successful design candidate is the same as was used for the kinematic synthesis of Stephenson II function generators, which is that the required accuracy points lie on a single trajectory of configurations without any singularities. This is determined by computing all the configurations of the linkage for a specified range of input angles.

The kinematics equations of the Stephenson III linkage are obtained from the loop equations as, $$\begin{aligned} L&=R(G-C)-(A+Q(D-A)+U(G-D))+C, \\ \overline{L}&=\overline{R}(\overline{G}-\overline{C})-(\overline{A}+\overline{Q}(\overline{D}-\overline{A})+\overline{U}(\overline{G}-\overline{D}))+\overline{C}, \\ M&=T(H-F)-(A+Q(D-A)+U(H-D))+(B+S(F-B))=0, \\ \overline{M}&=\overline{T}(\overline{H}-\overline{F})-(\overline{A}+\overline{Q}(\overline{D}-\overline{A})+\overline{U}(\overline{H}-\overline{D}))+(\overline{B}+\overline{S}(\overline{F}-\overline{B}))=0, \end{aligned} \tag{22}$$

which include the now known initial joint locations, $$\{A,\overline{A},B,\overline{B},C,\overline{C},D,\overline{D},F,\overline{F},G,\overline{G},H,\overline{H}\} \tag{23}$$

and the unknown joint angle parameters, $$\{Q,\overline{Q},R,\overline{R},S,\overline{S},T,\overline{T},U,\overline{U}\} \tag{24}$$

In the case that the angle ψ of Link BF is the input parameter, then the input x and output y variables are $$x=(S,\overline{S}),\ y=(Q,\overline{Q},R,\overline{R},T,\overline{T},U,\overline{U}), \tag{25}$$

and the analysis equations are $$F(x,y)=\begin{Bmatrix} L \\ \overline{L} \\ M \\ \overline{M} \\ Q\overline{Q}-1 \\ R\overline{R}-1 \\ T\overline{T}-1 \\ U\overline{U}-1 \end{Bmatrix}=\begin{Bmatrix} 0\\0\\0\\0\\0\\0\\0\\0 \end{Bmatrix} \tag{26}$$

These equations have six solutions for a specified input $x=(S,\overline{S})$ and are easily solved using the NSolve function in Mathematica. In the case that the angle ϕ of Link AD is the input parameter, then $x=(Q,\overline{Q})$ and Equations (25) and (26) change appropriately. The choice of input link provides different parameterizations of the same configuration space and will define different sets of singular configurations. Singular configurations are locations in the configuration space where $\det[J_F(x, y)]=0$, $$[J_F(x,y)] = \left[\frac{\partial F}{\partial y_1} \ \cdots \ \frac{\partial F}{\partial y_8}\right] \tag{27}$$

Singular configurations define the bounds of mechanism branches.

A set of input parameters $x_k$, k=1, . . . , n is generated that sweeps around the unit circle, $$x_k = \left\{\exp\left((i2\pi)\frac{k-1}{n-1}\right), \exp\left(-(i2\pi)\frac{k-1}{n-1}\right)\right\}, k=1, \ldots, n. \tag{28}$$

Equations (26) are solved for each $x_k$ to generate n sets of configurations, $$Ck=\{(x_k,y_{k,1}), \ldots, (x_k,y_{k,6})\}\ k=1, \ldots, n. \tag{29}$$

The members of $C_k$ for each k appear in no particular order, and the goal of this section is to sort configurations into separate trajectories as k is incremented from 1 to n.

The algorithm initializes by setting the six elements of $C_1$ as the beginning of six trajectories which are built upon by comparing $C_k$ to $C_{k+1}$ and deciphering pairs of connecting configurations, $$\begin{aligned} C_k&=\{(x_k,y_{k,p})|p=1, \ldots, 6\}, \\ C_{k+1}&=\{(x_{k+1},y_{k+1,q})|q=1, \ldots, 6\}, \end{aligned} \tag{30}$$

where in general configurations $(x_k, y_{k,p})$ and $(x_{k+1}, y_{k+1,q})$ connect such that p≠q. To decipher connections between $C_k$ and $C_{k+1}$, Newton's method is used to solve $F(x_{k+1}, y)=0$ for y using start points $y_{k,p}$, for p=1, . . . , 6. These approximate solutions are named $\tilde{y}_{k+1,p}$ where, $$\tilde{y}_{k+1,p}=y_{k,p}-[J_F(x_{k+1}, y_{k,p})]^{-1}F(x_{k+1}, y_{k,p}),$$

$$p=1, \ldots, 6 \tag{31}$$

is calculated from a single Newton iteration. Multiple iterations are used for more accuracy. The approximate configuration set $\tilde{C}_{k+1}$ is formed from $\tilde{y}_{k+1,p}$ where $$\tilde{C}_{k+1}=\{(x_{k+1},\tilde{y}_{k+1,p})|p-1, \ldots, 6|\} \tag{32}$$

Configuration $(x_k, y_{k,p})$ of $C_k$ connects to configuration $(x_{k+1}, y_{k+1,q})$ of $C_{k+1}$ if the following condition evaluates as true, $$|\tilde{y}_{k+1,p}-y_{k+1,q}|<tol, \tag{33}$$

where tol is a specified threshold value. For most k, configurations $C_k$ and $C_{k+1}$ will connect in a one to one fashion. However, Equation (33) allows the possibility that a configuration of $C_k$ will connect to several or none of the configurations of $C_{k+1}$, which is often the case near singularities. In these cases, the following logic can be employed:

1. If a configuration of $C_{k+1}$ is not connected to a configuration of $C_k$, that configuration of $C_{k+1}$ begins a new trajectory.

2. If a configuration of $C_k$ connects to multiple configurations of $C_{k+1}$, the trajectory associated with the configuration of $C_k$ is duplicated and each duplicate connects to a matching element of $C_{k+1}$.

3. If a configuration of $C_k$ does not connect to any configurations of $C_{k+1}$, the trajectory associated with the configuration of $C_k$ is concluded.

This procedure is executed for a complete sweep of the unit circle $x_k$, k=1, . . . , n, such that $x_n=x_1$. The result of this algorithm is a set of connected sequences of configurations that form separate mechanism trajectories. All combinations of these trajectories are checked for connections from k=n to k=1 configurations. If connections are identified, these trajectories are chained together to form longer trajectories.

Finally, configurations that do not correspond to rigid body movement are removed and the determinant of the Jacobian matrix along each trajectory is evaluated. A sign change indicates a change in trajectory that can arise from numerical error.

Once all trajectories have been assembled for a linkage design candidate, each is checked to see which and how many of the specified accuracy points they contain. A successful design candidate will produce a trajectory that moves through all 11 accuracy points. These designs are referred to herein as 11-point mechanisms.

While linkage designs that contain all 11 accuracy points on a single trajectory is the goal, the above-described design process identifies linkage designs with trajectories that move through less than 11 points as well. It is often the case that these mechanisms only slightly miss some accuracy points and may have other features useful to the designer, such as compact dimensions or reduced link overlap.

Figure 5:
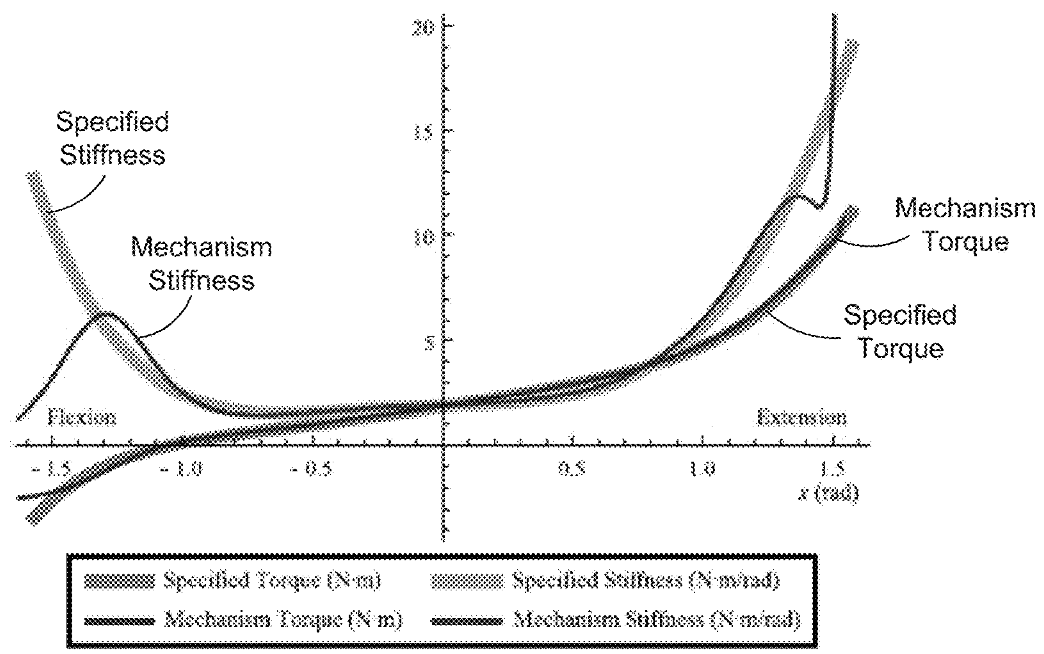
FIG. 5 is a graph that plots desired torque and stiffness profiles and the torque and stiffness profiles produced by the example mechanism.

As noted above, survivors of strokes often suffer from a muscle control disorder called spasticity which causes increased stiffness in muscles of joints such as the wrist. Measurement data of intrinsic wrist stiffness is illustrated in FIG. 5. The goal is to design a six-bar linkage that generates a specified torque profile that cancels spastic wrist stiffness.

The torque profile that the Stephenson III is to reproduce, and then cancel, can be derived from test data that measures the intrinsic stiffness profile in the wrists of stroke survivors. The test data of 21 such survivors was obtained and was least-squares fit with the following fifth degree polynomial, $$S(x)=0.3403347740344527x^5+2.3767146714792213x^4+1.4329074166324411x^3-0.21211179259258692x^2+0.5381754676253262x+1.903537638831755. \quad (34)$$

Because stiffness is the rate of change of a spring torque with respect to angular deflection, S(x) is integrated to obtain the torque profile, $$T(x)=\int S(x)dx+c_0=-0.056722462339075x^6+0.475342934295844x^5+0.358226854158110x^4-0.070703930864196x^3+0.269087733812663x^2+1.903537638831755x+1.859723104149862. \quad (35)$$

Equations (34) and (35) are graphed in FIG. 5. The integration constant of the torque profile was set such that $T(-\pi/3)=0$, which requires an unstable equilibrium at $x=-\pi/3$ rad. That means when the input link is rotated in the positive direction, a positive torque will act on it and will move the link away from the equilibrium position. Thus, this linkage will behave like a spring with "negative stiffness."

The use of a function generator to provide a required input torque profile begins with the assumption that there are no losses from friction, wear, and dynamic effects, which yields the power balance, $$T_{in}\dot{x}=T_{out}\dot{y}, \quad (36)$$

where $\dot{x}$ denotes the angular velocity of the input crank and $\dot{y}$ is the angular velocity of the output crank.

For this design, the output torque $T_{out}$ is generated by a torsion spring with stiffness k and equilibrium angle $y_e$, therefore the input torque is given by, $$T_{in}=-k(y-y_e)\frac{\dot{y}}{\dot{x}}=-k(y-y_e)\frac{dy}{dx}, \quad (37)$$

which is a function of the input angle x. Equation (37) can be solved for y=f(x) to obtain the set of input-output angles needed to design a Stephenson III function generator.

Separate variables and integrate to obtain, $$-\frac{1}{k}\int T_{in}(x)dx=\frac{1}{2}y^2-y_e y \quad (38)$$

and then solve for y to obtain, $$y=f(x)=\pm\sqrt{-\frac{2}{k}\int T_{in}(x)dx+y_e^2}+y_e. \quad (39)$$

The "+" and "−" solutions are two different functions that produce desired torque profile for given spring parameters k and $y_e$.

Figures 6A, 6B:
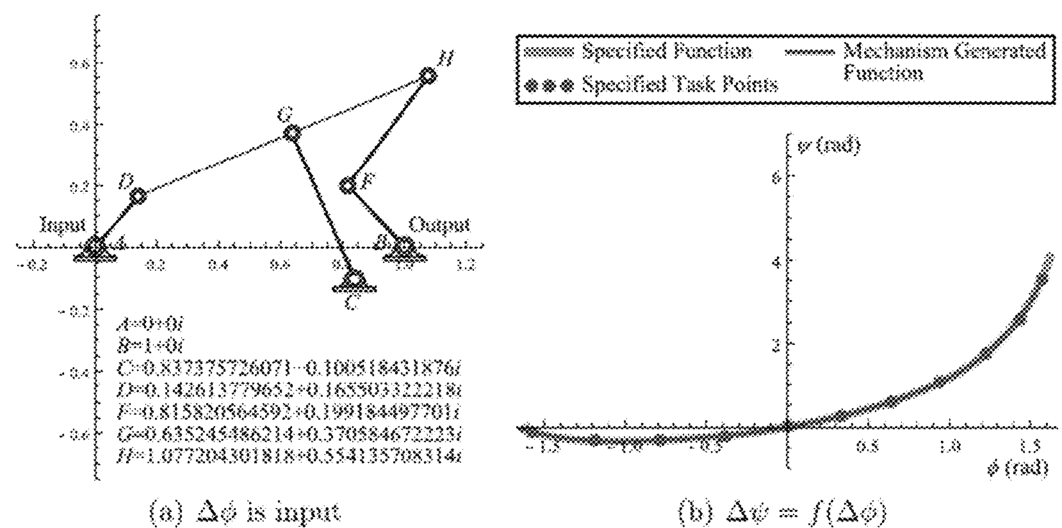
FIG. 6A is a schematic drawing of a Stephenson III linkage actuated by rotation of link AD.
FIG. 6B is a graph that shows the mechanized function of the linkage of FIG. 6A.

The input-output function for the synthesis of the Stephenson III function generator is obtained by substituting Equation (35) into Equation (39) with the requirement that k=0.45 N·m/rad and $y_e=2\pi$ rad. The "−" solution was taken to calculate the input-output y=f(x) function shown in FIGS. 6B and 6D.

This input-output function was evaluated at 11 positions of x to obtain the coordinated angles shown in Table. 1. Producing this function was investigated using both AD as the input, (x,y)=(Δϕ, Δψ), and BF as the input, (x, y)=(Δψ, Δϕ). The use of Bertini to obtain solutions to the synthesis equations is the same for both cases.

TABLE 1

Figure 6C:
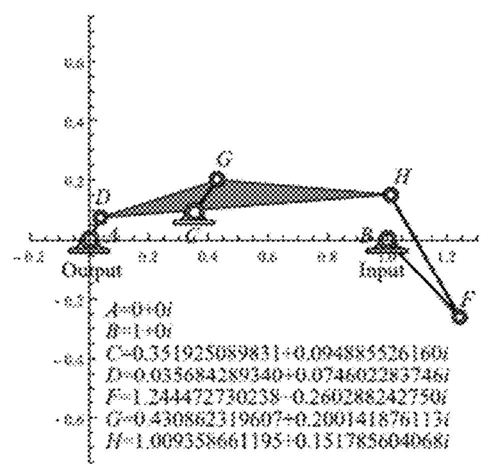
FIG. 6C is a schematic drawing of a Stephenson III linkage actuated by rotation of link BF.
Figure 6D:
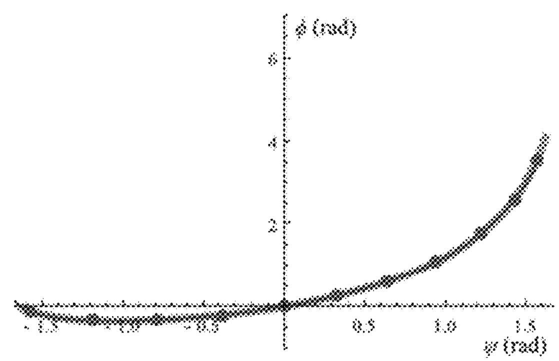
FIG. 6D is a graph that shows the mechanized function of the linkage of FIG. 6C.

Task position data as displayed in FIG. 6.

| j | $x_j$ | $y_j$ |
|---|---|---|
| 1 | −90° | −6.665566873543° |
| 2 | −68° | −19.185437363846° |
| 3 | −45° | −18.280827185669° |
| 4 | −22° | −11.558672810110° |
| 0 | 0° | 0° |
| 5 | 19° | 15.000375068384° |
| 6 | 37° | 34.756261256578° |
| 7 | 54° | 61.184689516866° |
| 8 | 70° | 99.804701760596° |
| 9 | 82° | 148.305746675651° |
| 10 | 90° | 203.021804302295° |

A summary of synthesis results is shown in Table 2. For the cases with φ as the input and ψ as the input, Bertini found 8,341 and 8,583 solutions that corresponded to physical linkages, respectively. Each solution set was then processed to add cognate solutions and remove solutions with very small or large link lengths such that 4,547 and 5,323 solutions were found for each case. The performance of these linkages was analyzed in order to categorize mechanisms by the number of accuracy points they can achieve in a singularity-free trajectory from 6 to 11 points. For φ as the input and ψ as the input, there were 96 and 109 mechanisms, respectively, that passed through all 11 points. The total computation time for each case was 5 hours and 7 hours performed on 64×2.2 GHz nodes of the University of California, Irvine High Performance Computing Cluster.

TABLE 2

Synthesis results for the cases of actuating Link AD, ψ f(φ), and actuating Link BF, φ = f(ψ).

| | ψ = f(φ) | φ = f(ψ) |
|---|---|---|
| Linkage solutions | 8341 | 8583 |
| Cognates added | 712 | 647 |
| Linkages analyzed | 4547 | 5323 |
| 11 point mechanisms | 96 | 109 |
| 10 point mechanisms | 225 | 131 |
| 9 point mechanisms | 352 | 333 |
| 8 point mechanisms | 450 | 596 |
| 7 point mechanisms | 793 | 887 |
| 6 point mechanisms | 1389 | 1104 |
| Synthesis computation time (hr) | 0.8 | 0.9 |
| Analysis computation time (hr) | 4.0 | 6.1 |

FIG. 6 shows two 11-point mechanisms and their input-output functions, one with φ as the input and one with ψ as the input. FIG. 5 shows the torque and stiffness profiles produced by the linkage shown in FIG. 6(*a*).

Figure 7A:
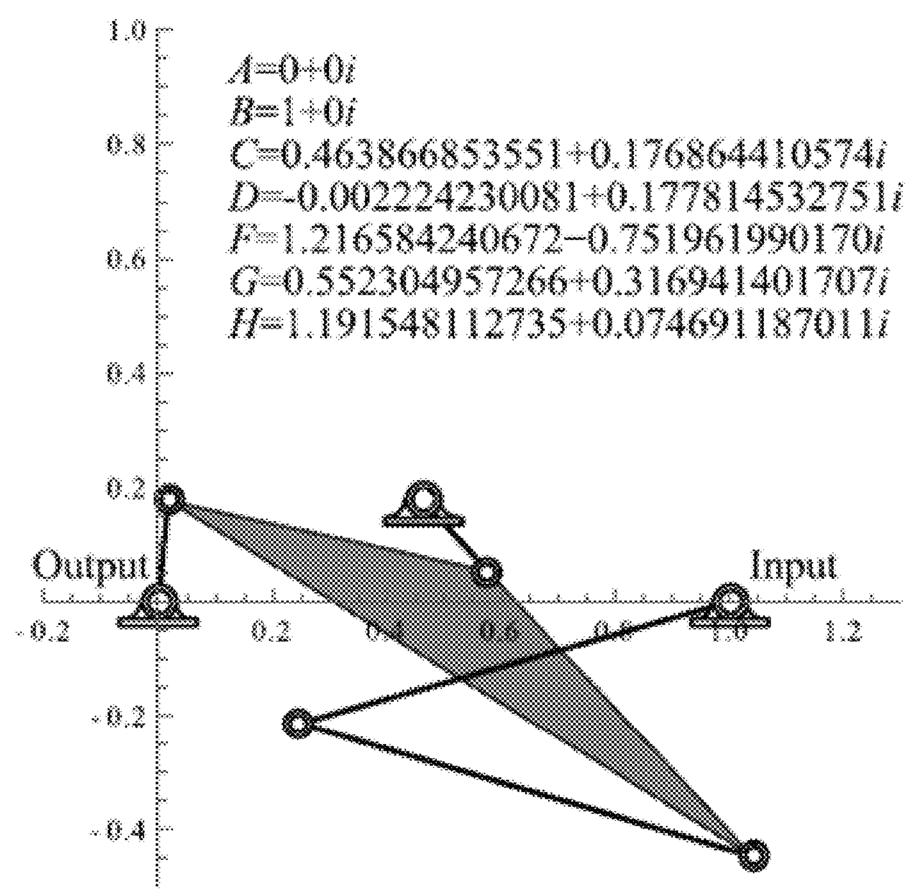
FIG. 7A is a schematic drawing of a defective linkage.
Figure 7B:
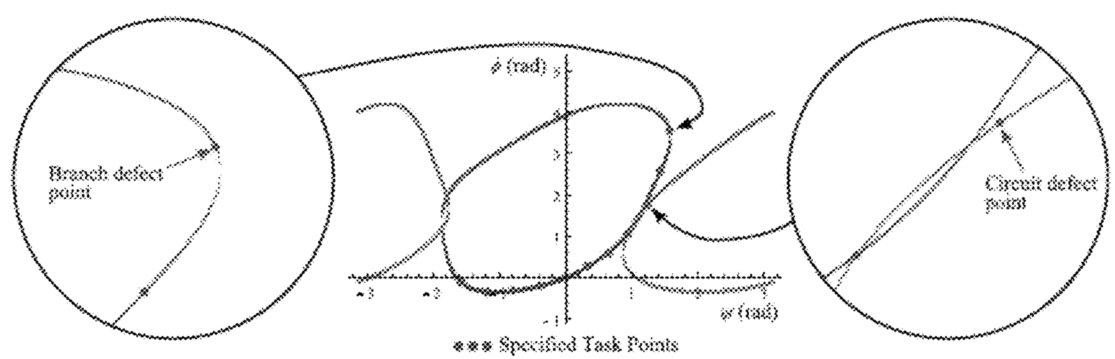
FIG. 7B is a graph that shows the configuration space of the linkage of FIG. 7A. A branch and circuit defect is illustrated.

FIG. 7 illustrates some common defects found in mechanisms that achieve less than 11 accuracy points. The figure depicts the configuration of a 9-point mechanism. Notice that one accuracy point is on a separate trajectory yielding a circuit defect. However, in the second case the accuracy point is on the same trajectory but separated from the others by a singularity, known as a branch defect. Despite these defects, the mechanism tracks the desired trajectory very closely and is useful to the designer.

The 11-point mechanism shown in FIG. 6A was integrated into a torque-compensating assistive wrist brace 10 shown in FIGS. 8-11, which can be worn by a stroke survivor (i.e., user) when performing rehabilitative exercises or when performing activities of daily living. As illustrated in FIGS. 8-11, which show the wrist brace 10 in various perspective views, the brace generally comprises a hand member 12 adapted to be provided on a user's hand, a forearm member 14 adapted to be provided on the user's forearm, and an assistive linkage 16 that connects the hand and forearm members and that provides a balancing torque to the wrist that counteracts, and potentially completely cancels, the intrinsic stiffness within the wrist that results from spasticity. Accordingly, the assistive linkage 16 can be said to apply a negative stiffness to the wrist that assists the user in rotating the wrist in both the flexion and extension directions, and further assists the user in maintaining a particular angular wrist position.

Figure 12:
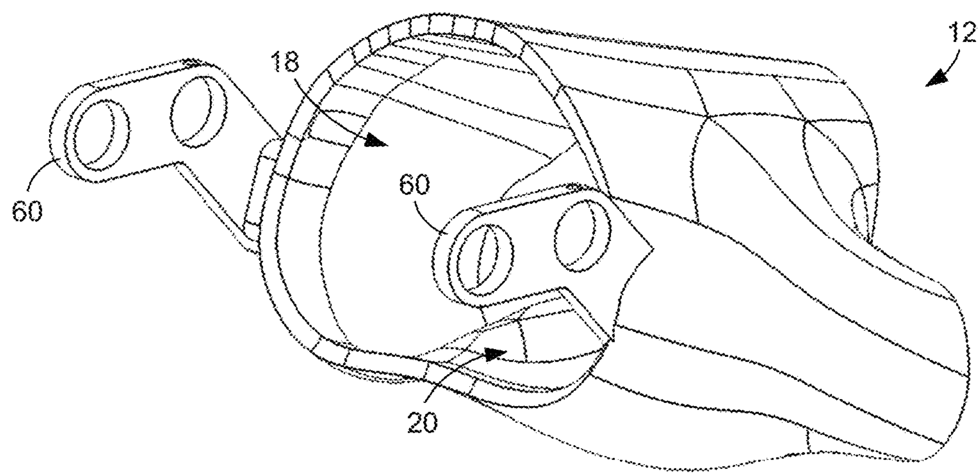
FIG. 12 is a perspective view of a hand member of the wrist brace of FIGS. 8-11.

FIG. 12 shows the hand member 12 separated from the remainder of the wrist brace 10, with the exception of two links that form part of the assistive linkage 16, which is described below. As indicated in FIG. 12, the hand member 12 can comprise a member that is sized and configured to receive and wrap around the user's hand. More particularly, the hand member 12 can comprise a continuous band having a relative wide finger passage 18 through which the user's fingers can pass and a smaller thumb passage 20 through which the user's thumb can separately pass. The band is shaped and configured to wrap all the way around the hand from the palm to the backside of the hand such the hand member 12 takes the form of a glove without fingers or a thumb. The hand member 12 can be made from various materials. Generally speaking, however, the hand member 12 is made of a material that has structural integrity so that forces applied by the hand to the hand member can be transmitted to the assistive linkage 16 and vice versa. In some embodiments, the hand member 12 is made of a polymeric material that can flex but has greater rigidity than a fabric.

Figure 13:
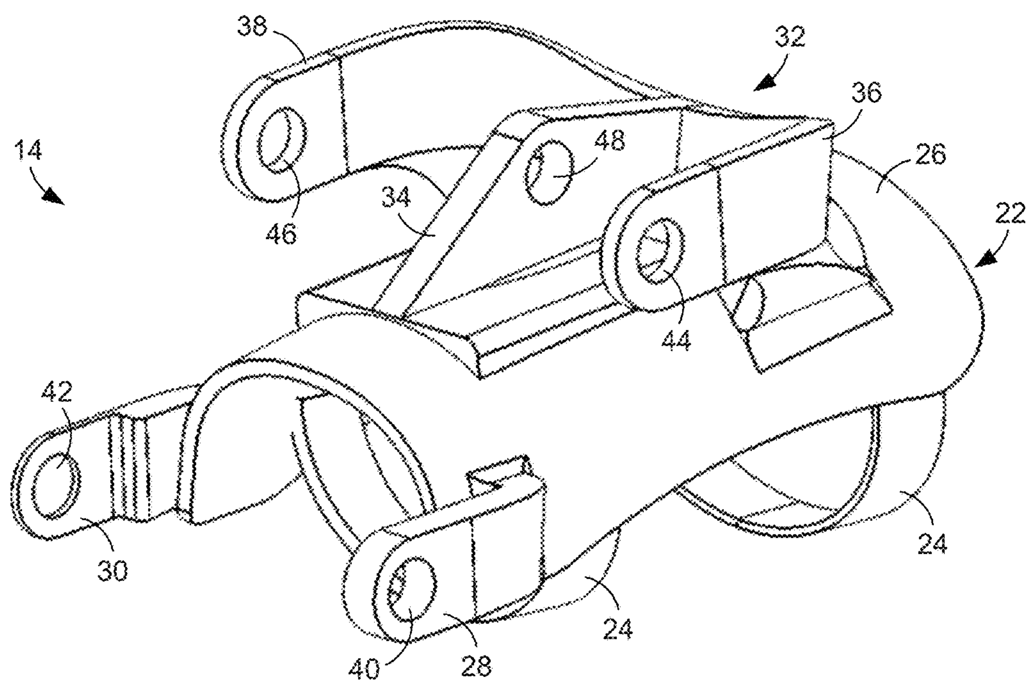
FIG. 13 is a perspective view of a forearm member of the wrist brace of FIGS. 8-11.

FIG. 13 shows the forearm member 14 separated from the reminder of the wrist brace 10. As shown in this figure, the forearm member 14 comprises a body 22 that is sized and configured to cover a top or outer side of the user's forearm and attachment straps 24 that are sized and configured to wrap around the bottom or inner side of the forearm to secure the member in place. In some embodiments, the body 22 comprises a curved shell that generally follows the contours of the forearm. Like the hand member 12, the body 22 of the forearm member 14 can be made of a material that has structural integrity, such as a polymeric material. The straps 24 can be made of a highly flexible material. In some embodiments, the straps 24 incorporate hook-and-loop fasteners (not shown) that enable adjustment of the forearm member 14 as well as application and removal of the member.

With further reference to FIG. 13, the forearm member 14 comprises multiple mounting elements that extend from a top or outer surface 26 of the body 22. These mounting elements form mounting and pivot points for various components of the assistive linkage 16 described below. In the illustrated embodiment, the mounting elements include a first pair of laterally spaced mounting arms 28 and 30 that extend forward from a distal end of the body 22 on opposed lateral sides of the body, and a top mounting element 32 provided on the top of the body that comprises a central longitudinal flange 34 that extends upward from the body and a second pair of laterally spaced mounting arms 36 and 38 that extend laterally from the longitudinal flange and then forward toward the distal end of the body. The first laterally spaced arms 28, 30 each comprise an opening 40, 42 provided at a distal end of the arm. As described below, these openings 40, 42 define the location of a pivot point for two links of the assistive linkage 16 as well as the axis about which the wrist pivots when the wrist brace 10 is worn. In similar manner, the second laterally spaced arms 26, 38 each comprise an opening 44, 46 provided at a distal end of the arm. As described below, these openings 44, 46 define the location of a pivot point for two other links of the assistive linkage 16. The longitudinal flange 34 also comprises an opening 48 that, as described below, is adapted to receive a transverse shaft 72 upon which two further links of the assistive linkage 16 are mounted. It is noted that the openings 40, 44, and 48, and the openings 42, 46, and 48, each define a ternary link of the assistive linkage 16. Accordingly, while the assistive linkage 16 is generally described as a component separate from the arm and forearm members 12, 14, the assistive linkage can be considered to comprise the portions of the mounting elements of the forearm member that define this ternary link. In some embodiments, the body 22 and the various mounting elements described above can be unitarily formed from a single piece of material.

The assistive linkage 16 will now be described with reference to FIGS. 8-11. As described above, the assistive linkage 16 is designed as a spring-assisted six-bar linkage having a configuration similar to that shown in FIG. 6A. The assistive linkage 16, however, actually comprises two such six-bar linkages, one provided on each side of the wrist. Beginning with the left side of the assistive linkage 16 (from the perspective of the wearer) shown in FIGS. 8 and 10, the first six-bar linkage includes a first binary link 50, a second binary link 52, a third binary link 54, a fourth binary link 56, a first ternary link 58, and a second ternary link formed by the mounting elements of the forearm member 14 and the openings 40, 44, and 48 (as described above in relation to FIG. 13). These links are connected together with various pivot elements 70, such as pivot pins or rivets, which extend through openings in the links (not numbered in the figures) that align with openings formed either in other links or the mounting elements of the forearm member. These pivot elements 70 define pivot points of the links of the assistive linkage 16.

Figure 8:
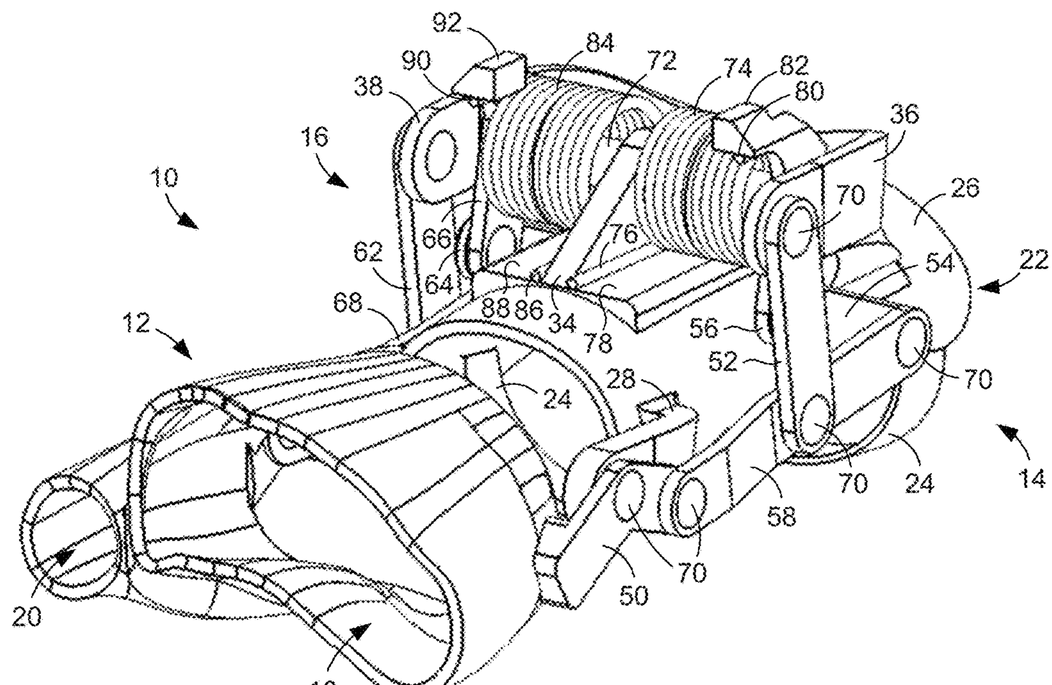
FIG. 8 is a top left perspective view of an embodiment of a wrist brace that incorporates an assistive linkage.
Figure 10:
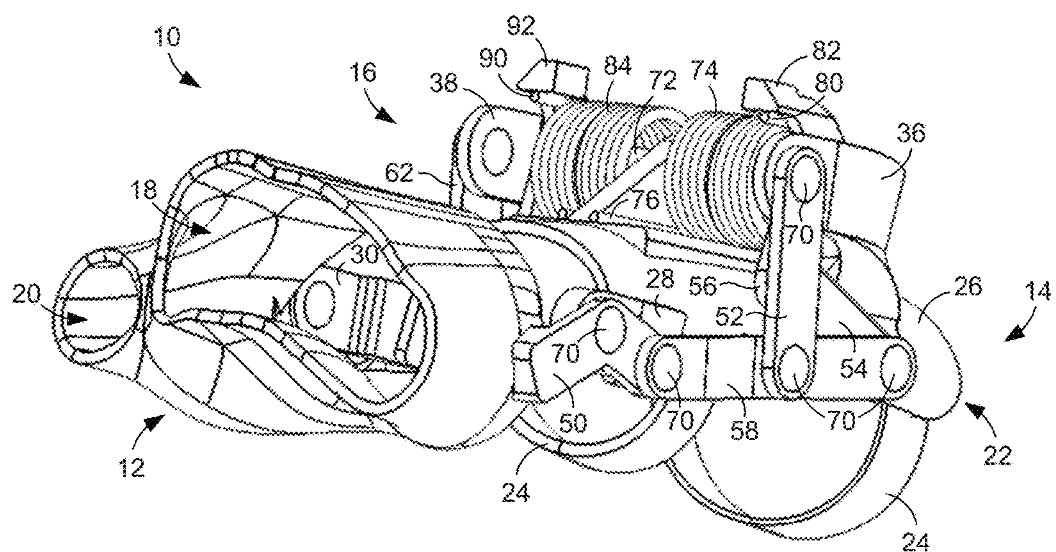
FIG. 10 is a bottom left perspective view of the wrist brace of FIGS. 8 and 9.

With further reference to FIGS. 8 and 10, the distal end of the first binary link 50 is fixedly mounted to the hand member 12 and the proximal end of the first binary link is pivotally connected to a distal end of the first ternary link 58. Positioned between the two ends of the first binary link 50 is a pivot point defined by the location of the opening 40 provided in the mounting arm 28 (see FIG. 13). This pivot point coincides with the pivot point of the wrist. The first ternary link 58 is pivotally connected at its proximal end to a proximal end (in the perspective of FIGS. 8 and 10) of the third binary link 54. Pivotally connected to the first ternary link 58 between its proximal and distal ends is a bottom end of the second binary link 52. The top end of the second binary link 52 is pivotally connected to the distal end of the mounting arm 36 at the location of the opening 44 (see FIG. 13). The distal end of the third binary link 54 is pivotally connected to the bottom end of the fourth binary link 56.

Figure 14:
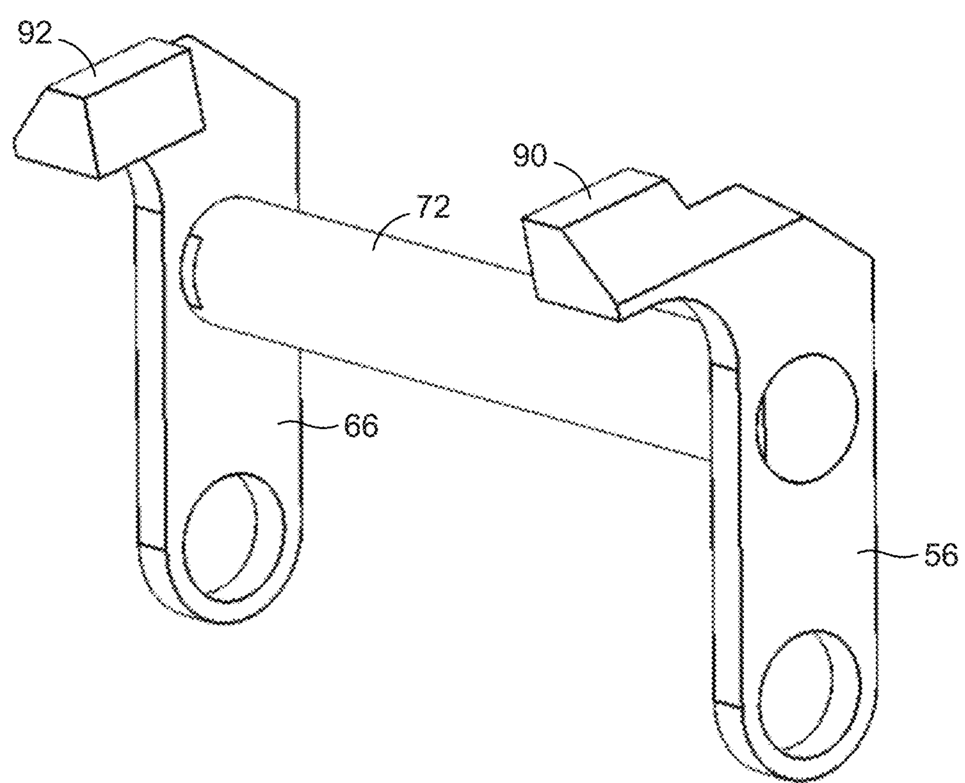
FIG. 14 is a perspective view of a shaft and two connected links of the wrist brace of FIGS. 8-11.

Unlike the other links, the fourth binary link 56 is pivotally mounted on a transverse shaft 72 that passes through the opening 48 provided in the central longitudinal flange 34. This shaft 72 is illustrated in FIG. 14. As is further shown in FIGS. 8 and 10, a biasing element 74, such as a torsion spring, surrounds the portion of the shaft 72 to the left of the flange 34 (from the perspective of the wearer). This biasing element 74 is held in torsional compression between the forearm member 14 and the fourth binary link 56. In the example embodiment of FIGS. 8-11, in which the biasing element 74 is a torsion spring, a first linear tang 76 at one end of the spring abuts a flat surface 78 formed on the top of the forearm member 14 and a second linear tang 80 at the opposite end of the spring abuts the underside of a stop 82 formed at the top end of the fourth binary link 56 (see FIG. 14). As such, the torsion spring applies torque to the forearm member and the fourth binary link 56.

As noted above, the right side of the assistive linkage 16 (from the perspective of the wearer) also comprises a six-bar linkage. This six-bar linkage, which is visible in FIGS. 9 and 11, also includes a first binary link 60, a second binary link 62, a third binary link 64, a fourth binary link 66, a first ternary link 68, and a second ternary link formed by the mounting elements of the forearm member 14 and the openings 42, 46, and 48 (as described above in relation to FIG. 13). These links are also connected together with various pivot elements 70, such as pivot pins or rivets, which extend through openings in the links (not numbered in the figures) that align with openings formed in either other links or the mounting elements of the forearm member.

Figure 9:
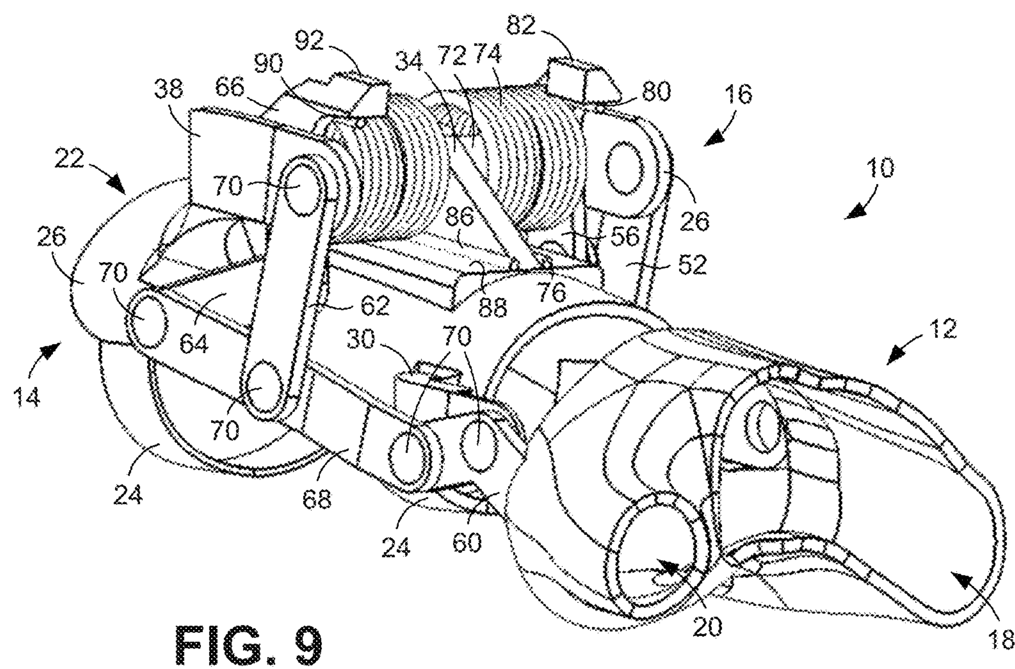
FIG. 9 is a top right perspective view of the wrist brace of FIG. 8.
Figure 11:
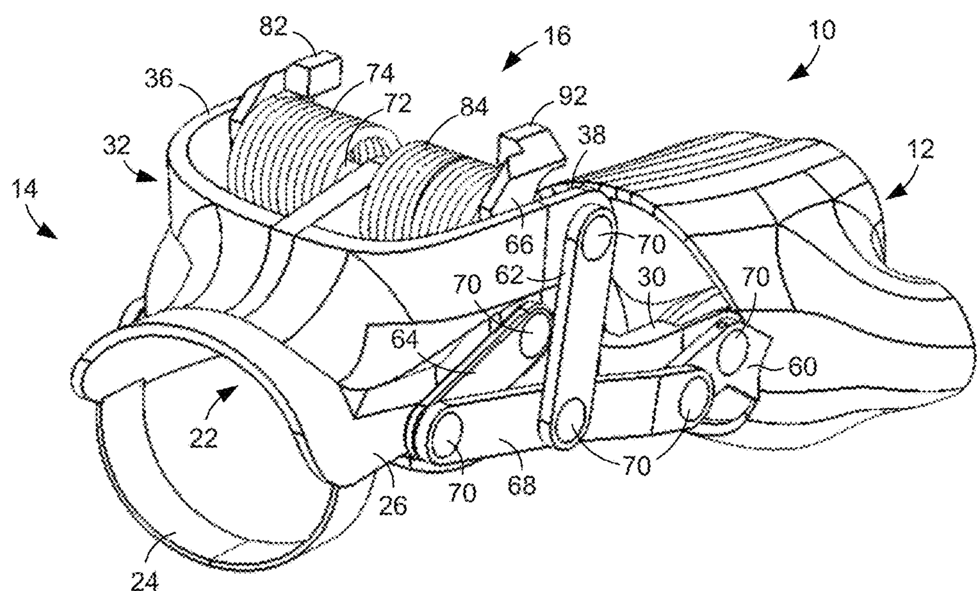
FIG. 11 is a further top right perspective view of the wrist brace of FIGS. 8-10.

With further reference to FIGS. 9 and 11, the distal end of the first binary link 60 is fixedly mounted to the hand member 12 and the proximal end of the first binary link is pivotally connected to a distal end of the first ternary link 68. Positioned between the two ends of the first binary link 60 is a pivot point defined by the location of the opening 42 provided in the mounting arm 30 (see FIG. 13). This pivot point coincides with the pivot point of the wrist. The first ternary link 68 is pivotally connected at its proximal end to a proximal end (in the perspective of FIGS. 9 and 11) of the third binary link 64. Pivotally connected to the first ternary link 68 between its proximal and distal ends is a bottom end of the second binary link 62. The top end of the second binary link 62 is pivotally connected to the distal end of the mounting arm 38 at the location of the opening 46 (see FIG. 13). The distal end of the third binary link 64 is pivotally connected to the bottom end of the fourth binary link 66.

Like the fourth binary link 56 of the left-side six-bar linkage, the fourth binary link 66 of the right-side six-bar linkage is pivotally mounted on the transverse shaft 72. As is further shown in FIGS. 9 and 11, a further biasing element 84, such as a torsion spring, surrounds the portion of the shaft 72 to the right of the flange 34 (from the perspective of the wearer). This biasing element 74 is held in torsional compression between the forearm member 14 and the fourth binary link 66. In the example embodiment of FIGS. 8-11, in which the biasing element 84 is a torsion spring, a first linear tang 86 at one end of the spring abuts a flat surface 88 formed on the top of the forearm member 14 and a second linear tang 90 at the opposite end of the spring abuts the underside of a stop 92 formed at the top end of the fourth binary link 66 (see FIG. 14).

Figure 15A:
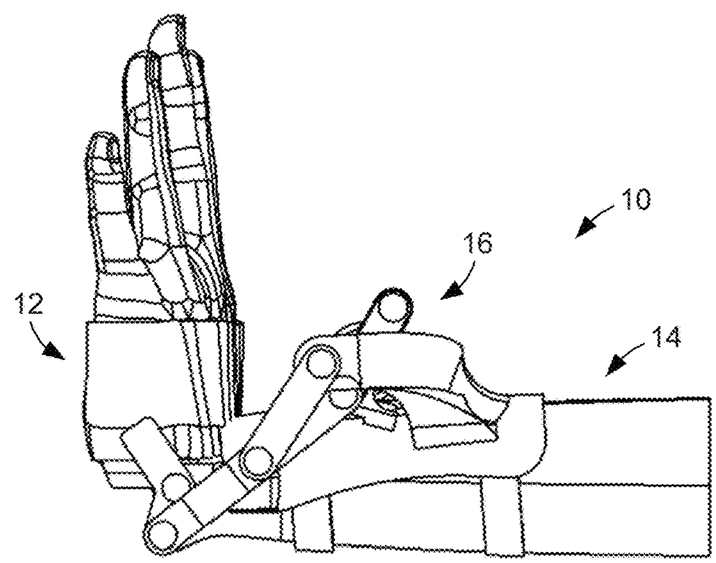
FIGS. 15A-15E are sequential side views of the wrist brace of FIGS. 8-11 as worn by a user while the wrist is pivoted from a maximum extension position to a maximum flexion position.
Figure 15B:
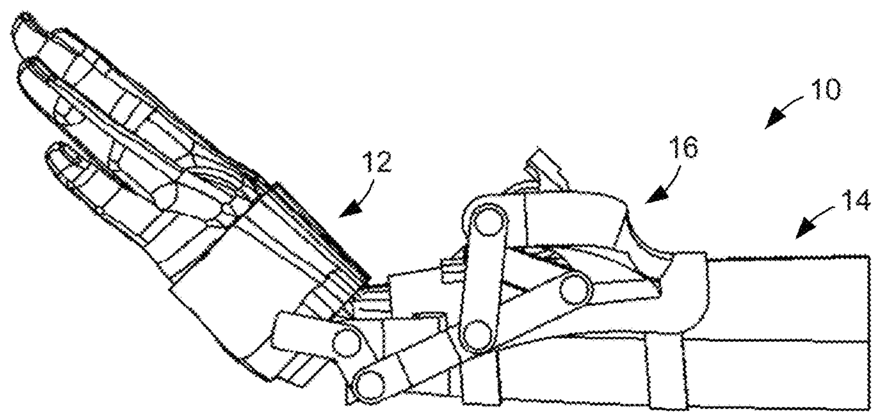
Figure 15C:
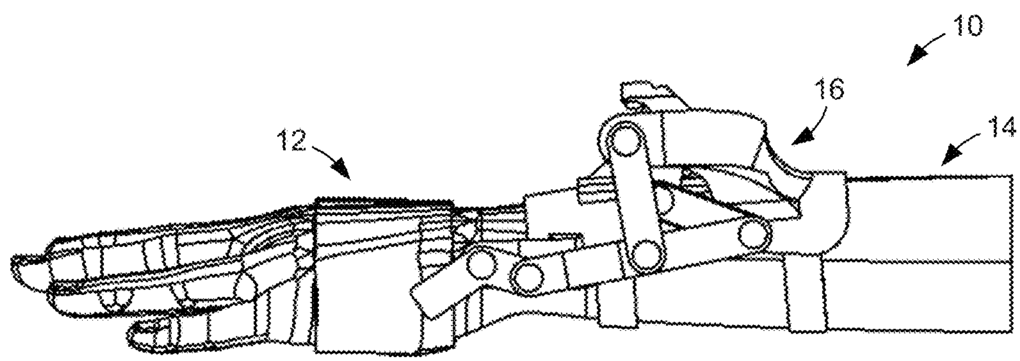
Figure 15D:
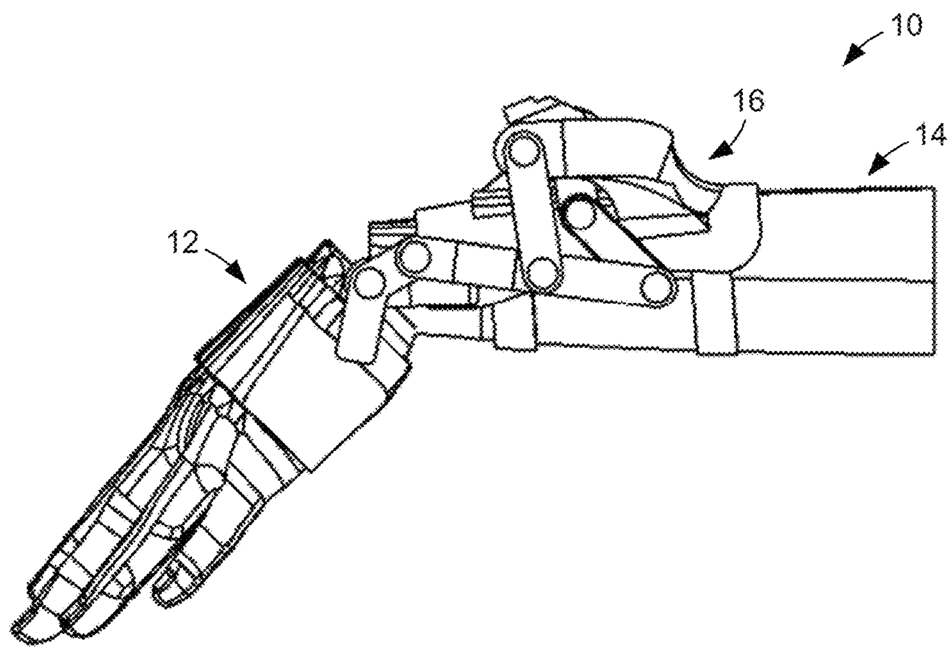
Figure 15E:
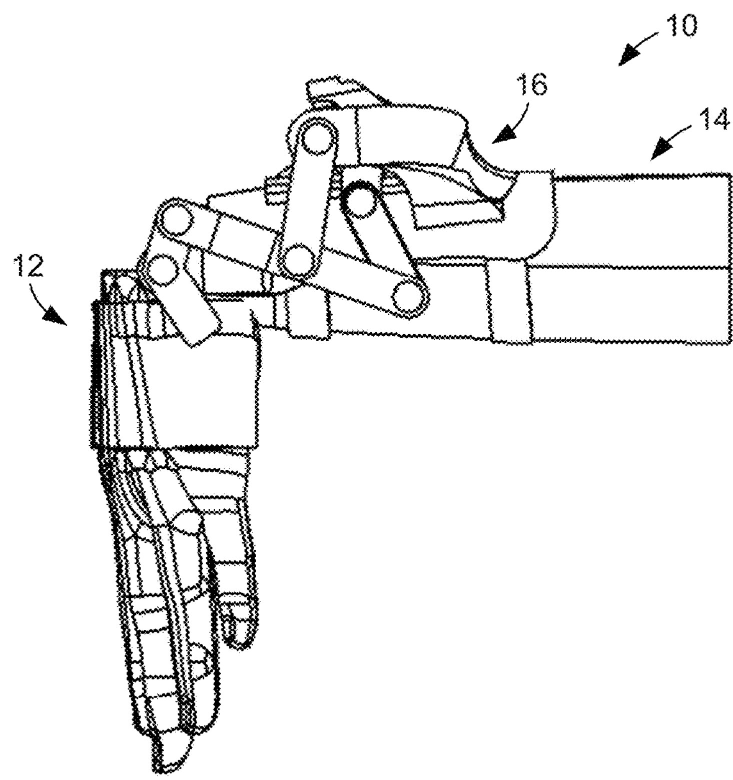
Figure 16:
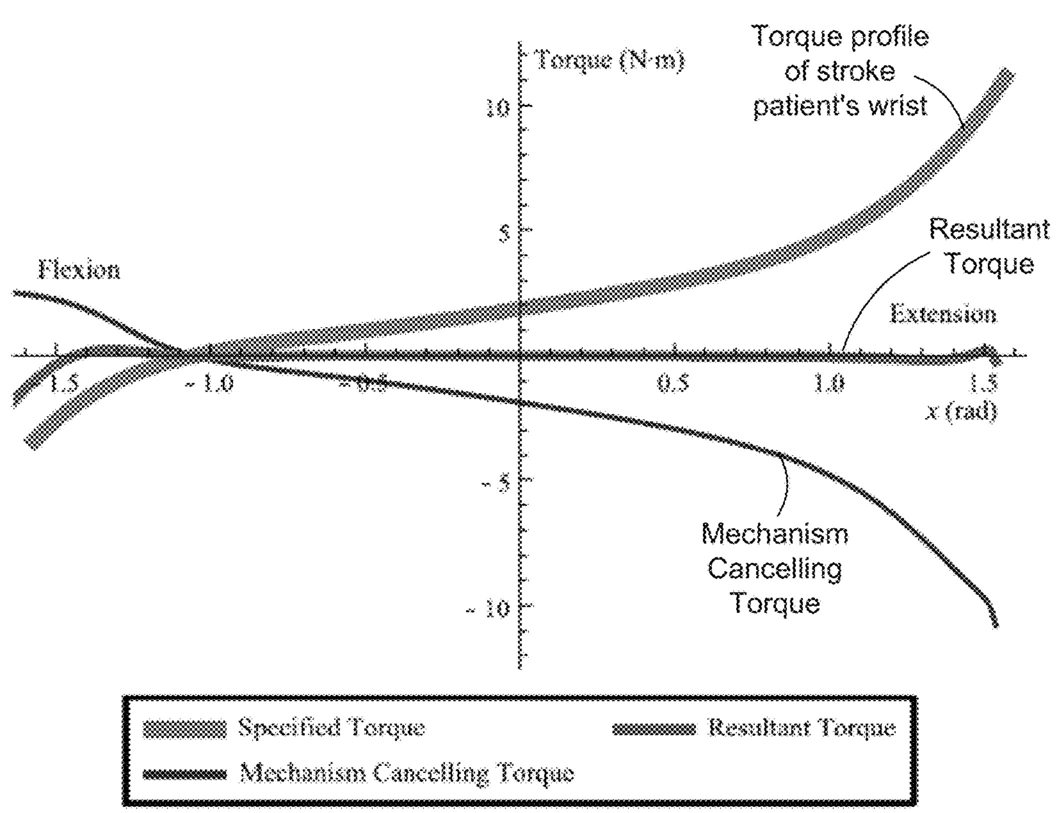
FIG. 16 is a graph that shows the resultant torque is near zero when an exemplary torque profile from a stroke patient's wrist and the torque exerted by the device of FIG. 15 are added.

FIGS. 15A-15E are sequential side views of the wrist brace 10 as worn by a user while the user is moving his or her wrist from a potential maximum extension point shown in FIG. 15A to a potential maximum flexion point shown in FIG. 15E. While it is unlikely that a stroke survivor would have this range of motion, the range is illustrated in FIGS. 15A-15E to illustrate operation of the wrist brace 10 and the movement of the various links of the assistive linkage 16. As is apparent from these figures, the various links pivot about their various pivot points (defined by the pivot elements 70). As the user's hand pivots about the wrist, the biasing elements 74, 84 (see FIGS. 8-11) apply an assistive torque to the hand that assists the user in moving the hand in the desired angular direction. Significantly, unlike prior art wrist braces, this assistive torque is provided in both the extension and flexion directions so that the inherent stiffness of the joint can be overcome in both directions. As described above, this assistive torque, or negative stiffness, can be substantially equal and opposite to the inherent torque or stiffness of the wrist so as to substantially cancel out that torque or stiffness. In some embodiments, the wrist brace 10 can cancel approximately 95% or more of the inherent torque or stiffness in each of the flexion and extension directions. This phenomenon is depicted in the graph of FIG. 16. Such a result is possible when the dimensions of the assistive linkage 16, including the lengths of its links and positions of its pivot points, are calculated in the manner described above based upon the individual's personal degree of spasticity, which can be determined through a medical examination. The result is that the user can pivot his or her wrist with much greater ease throughout its full range of motion, whatever that may be.

The invention claimed is:

1. A torque-compensating assistive wrist brace comprising:

a hand member adapted to attach to a user's hand, the hand member comprising a continuous band having a relative wide finger passage through which the user's fingers can pass and a smaller thumb passage through which the user's thumb can pass;

a forearm member adapted to attach to the user's forearm, the forearm member including a body and mounting elements provided on the body that form pivot points of the wrist brace; and an assistive linkage that connects the hand and forearm members together, the assistive linkage comprising one or more spring-assisted six-bar linkages and a transverse shaft, each spring-assisted six-bar linkage provided on a lateral side of the wrist brace, each spring-assisted six-bar linkage including four binary links, two ternary links, and a biasing element that together apply a balancing torque to a wrist of the user that counteracts intrinsic stiffness within the wrist and assists the user in rotating the wrist in both the flexion and extension directions;

wherein the mounting elements comprise a first pair of laterally spaced mounting arms that extend from a distal end of the body of the forearm member on opposed lateral sides of the body;

wherein the mounting elements further comprise a top mounting element that includes a central longitudinal flange that extends upward from the body and a second pair of laterally spaced mounting arms that extend laterally from the longitudinal flange and then forward toward the distal end of the body;

wherein the mounting arms each include an opening that defines a location of a pivot point for links of the one or more spring-assisted six-bar linkages, and wherein the central longitudinal flange includes an opening adapted to receive the transverse shaft upon which links of the one or more spring-assisted six-bar linkages are mounted;

wherein a first binary link of each spring-assisted six-bar linkage is fixedly attached to a lateral side of the hand member, pivotally connected to one of the mounting elements of the forearm member, and pivotally connected to a first ternary link of the corresponding spring-assisted six-bar linkage.

2. The assistive wrist brace of claim 1, wherein each first ternary link is pivotally connected to a second binary link and a third binary link of the corresponding spring-assisted six-bar linkage.

3. The assistive wrist brace of claim 2, wherein each second binary link is pivotally connected to one of the mounting elements of the forearm member.

4. The assistive wrist brace of claim 3, wherein each third binary link is pivotally connected to a fourth binary link of the corresponding spring-assisted six-bar linkage.

5. The assistive wrist brace of claim 4, wherein each biasing element comprises a torsion spring that applies torque to the body of the forearm member and to the corresponding fourth binary link.

* * * * *